US012491362B2

(12) United States Patent
Mulrooney

(10) Patent No.: US 12,491,362 B2
(45) Date of Patent: Dec. 9, 2025

(54) DEVICES, SYSTEMS, AND METHODS FOR TREATING AND PREVENTING DISEASE

(71) Applicant: Phagenesis Limited, Manchester (GB)

(72) Inventor: Conor Mulrooney, Manchester (GB)

(73) Assignee: Phagenesis Limited, Manchester (GB)

( * ) Notice: Subject to any disclaimer, the term of this patent is extended or adjusted under 35 U.S.C. 154(b) by 672 days.

(21) Appl. No.: 17/455,585

(22) Filed: Nov. 18, 2021

(65) Prior Publication Data

US 2022/0161030 A1 May 26, 2022

Related U.S. Application Data

(60) Provisional application No. 63/198,913, filed on Nov. 20, 2020.

(51) Int. Cl.
*A61N 1/36* (2006.01)
*A61N 1/05* (2006.01)

(52) U.S. Cl.
CPC ....... *A61N 1/36007* (2013.01); *A61N 1/0519* (2013.01)

(58) Field of Classification Search
CPC .............. A61N 1/36007; A61N 1/0519; A61N 1/3601; A61M 31/00
See application file for complete search history.

(56) References Cited

U.S. PATENT DOCUMENTS 3,839,841 A 10/1974 Amplatz
3,951,136 A 4/1976 Wall
(Continued)

FOREIGN PATENT DOCUMENTS

CA 2594296 A1 3/2006
CN 203389196 U 1/2014
(Continued)

OTHER PUBLICATIONS

Wilmskoetter, Janina , et al., "Cortical and Subcortical Control of Swallowing-Can We Use Information From Lesion Locations to Improve Diagnosis and Treatment for Patients With Stroke?", American journal of speech-language pathology vol. 29,2S (2020): 1030-1043. (Year: 2020).
(Continued)

*Primary Examiner* — Mark W. Bockelman
(74) *Attorney, Agent, or Firm* — Fortem IP LLP

(57) ABSTRACT

Devices, systems, and methods configured to treat disease using electrical stimulation and therapeutic agents are disclosed herein. In some embodiments, a device of the present technology comprises a first elongated shaft configured to deliver supplemental nutrition to a patient suffering from dysphagia and a second elongated shaft configured to slidably receive the first elongated shaft. The second elongated shaft can include one or more conductive elements configured to deliver electrical stimulation to nerves at a first treatment site in a pharynx of the patient. In some embodiments, the second elongated shaft includes one or more therapeutic elements carrying a therapeutic agent configured to be positioned at or adjacent a second treatment site with a pooled secretion in the patient's pharynx. The therapeutic agent can be configured to prevent or inhibit colonization of the pooled secretion by one or more pathogens. In some embodiments, the second elongated shaft includes a lumen fluidically coupled to an aperture extending through a sidewall of the elongated shaft. The aperture can be configured to be positioned at or adjacent the second treatment site with the pooled secretion. The lumen and aperture can be configured to transport fluid therethrough along a longitudinal dimension of the device to deliver a therapeutic agent to the second treatment site and/or withdraw the pooled secretion from the second treatment site into the lumen.

20 Claims, 9 Drawing Sheets

(56) References Cited

U.S. PATENT DOCUMENTS 4,453,545 A 6/1984 Inoue
4,776,349 A 10/1988 Nashef et al.
5,109,870 A 5/1992 Silny et al.
5,147,315 A 9/1992 Weber
5,179,952 A 1/1993 Buinevicius et al.
5,201,903 A 4/1993 Corbett et al.
5,372,131 A 12/1994 Heinen
5,389,074 A 2/1995 Parker et al.
5,551,953 A 9/1996 Lattin et al.
5,588,424 A 12/1996 Insler et al.
5,755,225 A 5/1998 Hutson
5,759,490 A 6/1998 Malchesky
5,762,638 A 6/1998 Shikani et al.
5,836,895 A 11/1998 Ramsey
5,957,968 A 9/1999 Belden et al.
6,006,138 A 12/1999 Don
6,148,222 A 11/2000 Ramsey
6,259,938 B1 7/2001 Zarychta et al.
6,266,548 B1 7/2001 Lamade et al.
6,366,813 B1 4/2002 Dilorenzo
6,464,697 B1 10/2002 Edwards et al.
6,484,053 B2 11/2002 Leelamanit et al.
6,532,388 B1 * 3/2003 Hill ...................... A61N 1/0556 607/9
6,611,699 B2 8/2003 Krueger
6,613,025 B1 9/2003 Palasis
6,658,294 B1 12/2003 Zadeh et al.
6,856,822 B2 2/2005 Larsson
7,324,851 B1 1/2008 Dilorenzo
7,598,839 B1 10/2009 Wedley
7,871,430 B2 1/2011 Pavcnik et al.
8,048,062 B2 11/2011 Adams et al.
8,092,433 B2 1/2012 Hamdy
8,876,798 B2 11/2014 Clark et al.
8,968,331 B1 3/2015 Sochor
10,028,885 B2 7/2018 Martin et al.
10,743,810 B2 8/2020 Mulrooney
11,617,881 B2 4/2023 Mulrooney et al.
11,980,753 B2 5/2024 Mulrooney et al.
11,992,681 B2 5/2024 Mulrooney
2001/0054425 A1 12/2001 Bertram
2002/0032468 A1 3/2002 Hill et al.
2002/0065544 A1 5/2002 Smits
2002/0177765 A1 11/2002 Bowe et al.
2003/0036794 A1 2/2003 Ragheb et al.
2004/0034396 A1 2/2004 Asmar et al.
2004/0073110 A1 4/2004 Stewart et al.
2004/0162584 A1 8/2004 Hill et al.
2004/0220645 A1 11/2004 Kretschmer et al.
2004/0230162 A1 11/2004 Tan
2005/0137459 A1 6/2005 Chin et al.
2005/0192559 A1 9/2005 Michels et al.
2005/0229933 A1 10/2005 Mcgrail et al.
2006/0085049 A1 4/2006 Cory et al.
2007/0074728 A1 4/2007 Rea
2007/0089898 A1 4/2007 Potter
2007/0156041 A1 7/2007 Rea
2008/0009810 A1 * 1/2008 Hamdy .............. A61N 1/36007 607/40
2008/0147013 A1 6/2008 Breton et al.
2008/0249507 A1 10/2008 Hadani
2008/0255441 A1 10/2008 Hadani
2008/0300530 A1 12/2008 Massengale
2009/0062772 A1 3/2009 Wakeford et al.
2009/0223698 A1 9/2009 Gilliland et al.
2009/0276025 A1 11/2009 Burnes et al.
2010/0115739 A1 5/2010 Mathur
2010/0170066 A1 7/2010 Honeycutt
2010/0174170 A1 7/2010 Razavi
2010/0206453 A1 8/2010 Leeflang et al.
2010/0218975 A1 9/2010 Mehan
2010/0317956 A1 12/2010 Kartush
2011/0137374 A1 6/2011 Kieval et al.
2011/0210215 A1 9/2011 Nitsche et al.
2011/0251519 A1 10/2011 Romoscanu
2012/0065469 A1 3/2012 Allyn et al.
2012/0203058 A1 8/2012 Kanapkey et al.
2012/0259208 A1 10/2012 Bloom et al.
2012/0260921 A1 10/2012 Sangwan
2013/0006323 A1 1/2013 Tal et al.
2013/0197321 A1 8/2013 Wilson
2013/0282078 A1 10/2013 Wacnik
2014/0012235 A1 1/2014 Pinchuk et al.
2014/0128936 A1 5/2014 Laufer et al.
2014/0276663 A1 9/2014 Pinchuk et al.
2014/0288382 A1 * 9/2014 Lemmens ............ A61B 5/4884 600/300
2014/0288384 A1 9/2014 Mulrooney
2014/0303617 A1 10/2014 Shimada
2014/0378941 A1 12/2014 Su et al.
2015/0224280 A1 8/2015 Pinchuk et al.
2017/0050014 A1 2/2017 Rizik
2017/0224986 A1 8/2017 Imran et al.
2017/0312497 A1 11/2017 Mulrooney et al.
2018/0235533 A1 8/2018 Mulrooney
2019/0038894 A1 2/2019 Bassi et al.
2019/0134380 A1 5/2019 Mulrooney
2019/0134389 A1 5/2019 Mulrooney
2020/0061369 A1 2/2020 Mulrooney et al.
2020/0061370 A1 2/2020 Mulrooney et al.
2020/0179045 A1 6/2020 Levin et al.
2020/0306528 A1 10/2020 Linden et al.
2020/0330025 A1 10/2020 Mulrooney
2021/0077808 A1 3/2021 Mulrooney et al.
2022/0160537 A1 5/2022 Mulrooney
2022/0161029 A1 5/2022 Mulrooney
2022/0161030 A1 * 5/2022 Mulrooney .......... A61N 1/3601
2022/0313981 A1 10/2022 Mulrooney
2023/0181023 A1 6/2023 Mulrooney
2023/0302244 A1 9/2023 Mulrooney
2023/0405324 A1 12/2023 Mulrooney
2024/0009451 A1 1/2024 Mulrooney
2024/0299746 A1 9/2024 Mulrooney

FOREIGN PATENT DOCUMENTS

| | | | |
|---|---|---|---|
| CN | 203954394 | U | 11/2014 |
| CN | 204319485 | U | 5/2015 |
| EP | 0510857 | A1 | 10/1992 |
| EP | 0571514 | A1 | 12/1993 |
| EP | 1179307 | A2 | 2/2002 |
| EP | 2693968 | A1 | 2/2014 |
| GB | 2169206 | A | 7/1986 |
| GB | 2254253 | A | 10/1992 |
| GB | 2294642 | A | 5/1996 |
| GB | 2313316 | A | 11/1997 |
| GB | 2532044 | A | 5/2016 |
| GB | 2541039 | A | 2/2017 |
| JP | 5115563 | A | 5/1993 |
| JP | 2556694 | B2 | 11/1996 |
| JP | 2005312969 | A | 11/2005 |
| JP | 2012512722 | A | 6/2012 |
| JP | 2014068716 | A | 4/2014 |
| WO | 9400050 | A1 | 1/1994 |
| WO | 9405361 | A1 | 3/1994 |
| WO | 9526777 | A1 | 10/1995 |
| WO | 9715349 | A1 | 5/1997 |
| WO | 9719667 | A1 | 6/1997 |
| WO | 03026741 | A1 | 4/2003 |
| WO | 2006024825 | A1 | 3/2006 |
| WO | 2007129002 | A1 | 11/2007 |
| WO | 2009154718 | A1 | 12/2009 |
| WO | 2010023579 | A1 | 3/2010 |
| WO | 2010071812 | A1 | 6/2010 |
| WO | 2010091440 | A2 | 8/2010 |
| WO | 2012131303 | A1 | 10/2012 |
| WO | 2014152808 | A1 | 9/2014 |
| WO | 2015027094 | A1 | 2/2015 |
| WO | 2017089752 | A1 | 6/2017 |

(56) References Cited

FOREIGN PATENT DOCUMENTS

| | | | |
|---|---|---|---|
| WO | 2022106843 | A1 | 5/2022 |
| WO | 2022106844 | A1 | 5/2022 |

OTHER PUBLICATIONS

Bath et al., Pharyngeal electrical stimulation for neurogenic dysphagia following stroke, traumatic brain injury or other causes: Main results from the PHADER cohort study, EClinical Medicine 28 (2020) 100608, 9 pages.
Bath et al., Pharyngeal Electrical Stimulation for Treatment of Dysphagia in Subacute Stroke A Randomized Controlled Trial, Stroke, Jun. 2016, vol. 47, Issue 6, pp. 1562-1570.
Dziewas et al., Design and implemental of Pharyngeal electrical Stimulation for early de-cannulation in TRACheotomized (PHAST-TRAC) stroke patients with neurogenic dysphagia, International Journal of Stroke, 12(4), 2017, pp. 430-437.
Dziewas et al., PHAryngeal electrical STimulation for early decannulation in TRACheotomised patients with neurogenic dysphagia after stroke (PHAST-TRAC): a prospective, single-blinded, randomised trial, Lancet Neurology, vol. 17, Issue 10, 2018, 29 pages.
Essa et al., The BDNF polymorphism VAL66Met may be predictive of swallowing improvement post pharyngeal electrical stimulation in dysphagic stroke patients, Neurogastroenterol Motil, 2017, 27, 7 pages.
Fraser et al., Differential changes in human pharyngoesophageal motor excitability induced by swallowing, pharyngeal stimulation, and anesthesia, Am J Physiol Gastrointest Liver Physiol, 285: G-137-G144, 2003.
Hamdy et al., The cortical topography of human swallowing musculature in health and disease, Nature Medicine, vol. 2, No. 11, Nov. 1996, pp. 1217-1224.
Hamdy, et al., Long-term reorganization of human motor cortex driven by short-term sensory stimulation, Nature Neuroscience, vol. 1, No. 1, May 1998, pp. 64-68.
European Patent Office, International Search Report and Written Opinion for International Application No. PCT/GB2021/053010, Feb. 23, 2022, 13 pages.
European Patent Office, International Search Report and Written Opinion for International Application No. PCT/GB2021/053011, Feb. 24, 2022, 16 pages.
European Patent Office, International Search Report and Written Opinion for International Application No. PCT/GB2017/051482, Jul. 24, 2017, 8 pages.
European Patent Office, International Search Report and Written Opinion for International Application No. PCT/GB2016/053628, Mar. 15, 2017, 12 pages.
European Patent Office, International Search Report and Written Opinion for International Application No. PCT/GB2015/053366, Jan. 29, 2016, 13 pages.
Jayasekeran et al., Adjunctive Functional Pharyngeal Electrical Stimulation Reverses Swallowing Disability After Brain Lesions, Gastroenterology, 2010, vol. 138, No. 5, pp. 1737-1746.
Koestenberger et al., A Pilot Study of Pharyngeal Electrical Stimulation of Orally Intubated ICU Patients with Dysphagia, Neurocrit Care (2020) 32: 532-538.
Magara et al., Tu1254 Does Combining Pharyngeal Electrical Stimulation With Simultaneous Swallowing of Carbonated Liquids Enhance the Cortical Swallowing Motor System?, Gastroenterology, Apr. 2016 [Abstract only].
Magara et al., Exploring the effects of synchronous pharyngeal electrical stimulation with swallowing carbonated water on cortical excitability in the human pharyngeal motor system, Neurogastroenterol Motil (2016), 11 pages.
European Patent Office, International Search Report and Written Opinion for International Application No. PCT/GB2016/052389, Nov. 2, 2016, 15 pages.
Restivo et al., Pharyngeal electrical stimulation device for the treatment of neurogenic dysphagia: technology update, Medical Devices: Evidence and Research, 2018: 11, pp. 21-26.
Restivo et al., Pharyngeal Electrical Stimulation for Dysphagia Associated with Multiple Sclerosis: A Pilot Study, Brain Stimulation 6, 2013, pp. 418-423.
Sasegbon et al., Advances in the Use of Neuromodulation for Neurogenic Dysphagia: Mechanisms and Therapeutic Application of Pharyngeal Electrical Stimulation, Transcranial Magnetic Stimulation, and Transcranial Direct Current Stimulation, American Journal of Speech-Language Pathology, Jul. 2020, vol. 29, pp. 1044-1064.
Scutt et al., Pharyngeal Electrical Stimulation for Treatment of Poststroke Dysphagia: Individual Patient Data Meta-Analysis of Randomised Controlled Trials, Stroke Research and Treatment, 2015, 8 pages.
Suntrup et al., Electrical pharyngeal stimulation for dysphagia treatment in tracheotomized stroke patients: a randomized controlled trial, Intensive Care Med (2015) 41: 1629-1637.
Suntrup-Krueger et al., Electrical pharyngeal stimulation increases substance P level in saliva, Neurogastroenterol Motil (2016) 28, pp. 855-860.
Vasant et al., Pharyngeal Electrical Stimulation in Dysphagia Poststroke: A Prospective, Randomized Single-Blinded Interventional Study, Neurorehabilitation and Neural Repair, 2016, vol. 30(9), pp. 866-875.
European Patent Office, International Search Report and Written Opinion for International Application No. PCT/GB2005/003289, Dec. 30, 2005, 14 pages.
Fraser et al., "Driving Plasticity in Human Adult Motor Cortex is Associated with Improved Motor Function After Brain Injury", Neuron, vol. 34, May 30, 2002, pp. 831-840.
Gow et al., "Characterising the Central Mechanisms of Sensory Modulation in Human Swallowing Motor Cortex", Clinical Neurophysiology, Elsevier Science, IE, vol. 115, No. 10, Jun. 26, 2004, pp. 2382-2390.
Hamdy et al., "Modulation of human swallowing behaviour by thermal and chemical stimulation in health and after brain injury", Neurogastroenterol Motil, vol. 15, No. 1, Feb. 2003, pp. 69-77.
Hamdy et al., "Recovery of Swallowing After Dysphagic Stroke Relates to Functional Reorganization in the Intact Motor Cortex", Gastroenterology, vol. 115, No. 5, Nov. 1998, pp. 1104-1112.
Jasper, Herbert H., "The Ten Twenty Electrode System of the International Federation", International Federation, pp. 370-375.
Kajii et al., "Sour taste stimulation facilitates reflex swallowing from the pharynx and larynx in the rat", Physiology & Behavior, vol. 77, No. 2-3, 2002, pp. 321-325.
Takeuchi et al., "Electrophysiological and Behavioral Studies of Taste Discrimination in the Axolotl (*Ambystoma mexicanum*)", Physiology & Behavior, vol. 56, No. 1, Jul. 1994, pp. 121-127.
Tutuian et al., "Effects of position on oesophageal function: studies using combined manometry and multichannel intraluminal impedance", Neurogastroenterol Motil., vol. 15, No. 1, Feb. 2003, pp. 63-67.
Wassermann, Eric M., "Risk and safety of repetitive transcranial magnetic stimulation: report and suggested guidelines from the International Workshop on the Safety of Repetitive Transcranial Magnetic Stimulation, Jun. 5-7, 1996", Electroencephalography and clinical Neurophysiology, vol. 108, 1998, pp. 1-16.
Takeishi, et al., "Effects of Pharyngeal Electrical Stimulation on Swallowing Performance", PLOS ONE 13(1): e0190608. https://doi.org/10.1371/journal.pone.0190608 (Year: 2018).

* cited by examiner

FIG. 3A
Nasal Cavity
100
Nasopharynx
104
External Naris
Body of Tongue
Pharynx
Posterior Wall
Oropharynx
Epiglottis
108
Valeculla
108
Laryngopharynx
UES
Larynx
102

DEVICES, SYSTEMS, AND METHODS FOR TREATING AND PREVENTING DISEASE

CROSS-REFERENCE TO RELATED APPLICATION(S)

The present application claims the benefit of priority to U.S. Provisional Patent Application No. 63/198,913, titled DEVICES, SYSTEMS, AND METHODS FOR TREATING AND PREVENTING DISEASE, filed Nov. 20, 2020, which is incorporated by reference herein in its entirety.

TECHNICAL FIELD

The present disclosure is directed generally to devices, systems, and methods for treating and preventing disease. Particular embodiments include treating dysphagia by applying electrical stimulation to a target neural population of the patient.

BACKGROUND

Dysphagia is the condition whereby a patient has difficulty in swallowing or is unable to swallow safely. Dysphagia may be caused, for example, by stroke, neurodegenerative diseases, brain tumors or in some cases by other co-morbidities, such as respiratory disorders. It has been reported that between 7 and 10% of all adults older than 50 years of age present with clinically significant dysphagia. Of those over the age of 60, this increases to 14%. In total, 10 million Americans are evaluated each year in clinics and hospitals for swallowing difficulties. It has also been reported that over 51% of institutionalized elderly patients present with oropharyngeal dysphagia.

Swallowing is a rigidly ordered sequence of events that results in the propulsion of food from the mouth through the pharynx and esophagus to the stomach. At the same time, respiration is inhibited and food is prevented from entering into the trachea. Swallowing can be initiated voluntarily, but thereafter it is almost entirely under reflex control. The swallow reflex is typically initiated by sensory impulses from tactile receptors (particularly those located near the opening of the pharynx) being transmitted to certain areas in the medulla. The central integrating areas for swallowing lie in the medulla and lower pons; they are collectively called the swallowing center. Motor impulses travel from the swallowing center to the musculature of the pharynx and upper esophagus via various cranial nerves. This lower swallowing center in the brainstem is under regulatory control by higher center in the cerebral cortex. These higher swallowing centers or regions control the voluntary initiation and modulation of the swallow.

Swallowing occurs in three stages. In the oral or voluntary phase, food is moved towards the back of the mouth by the tongue, and forced into the pharynx, where it stimulates the tactile receptors that initiate the swallowing reflex. In the pharyngeal stage of swallowing, food passes through the pharynx by constriction of the walls of the pharynx, backward bending of the epiglottis, and an upward and forward movement of the larynx and trachea. During the pharyngeal stage, respiration is reflexively inhibited. In the esophageal stage of swallowing, food moves down the esophagus and into the stomach, assisted by one or more peristaltic waves.

Although the main function of swallowing is the propulsion of food from the mouth into the stomach, swallowing also serves as a protective reflex for the upper respiratory tract, preventing unwanted particles from entering the tract.

Food or liquid that enters into the airways may act as a locus for infection and this type of infection can be life threatening. For instance, dysphagia after a stroke can be a devastating problem, as it carries a six-fold increased risk of aspiration pneumonia.

Complications that have been associated with dysphagia include pneumonia, malnutrition, dehydration, poorer long-term outcome, increased length of hospital stay, increased rehabilitation time and the need for long-term care assistance, increased mortality, and increased health care costs. These complications impact the physical and social wellbeing of patients, quality of life of both patients and caregivers, and the utilization of health care resources.

In view of the above, there remains a need for improved devices and methods that can treat dysphagia.

SUMMARY

The present technology relates to electrical stimulation devices and associated systems and methods. In particular embodiments, the present technology comprises electrical stimulation devices configured to perform pharyngeal electrical stimulation (PES) to treat one or more conditions. Several embodiments of the present disclosure, for example, are configured to perform PES to treat a patient suffering from neurogenic dysphagia. Electrical stimulation of nerves proximate the patient's pharynx increases activity in the motor cortex and other areas of the brain to facilitate a functional reorganization of the centers in the brain responsible for controlling and coordinating swallow function. In some embodiments, the present technology is configured to reduce a patient's risk of developing aspiration pneumonia by removing a pharyngeal substance from the patient's pharynx and/or preventing or inhibiting colonization of the pharyngeal substance by one or more pathogens. The subject technology is illustrated, for example, according to various aspects described below, including with reference to FIGS. 1-6. Various examples of aspects of the subject technology are described as numbered clauses (1, 2, 3, etc.) for convenience. These are provided as examples and do not limit the subject technology.

1. A device for delivering an electrical stimulus to nerves proximate a body lumen of a human patient, the device comprising:
   - a first elongated shaft;
   - a second elongated shaft defining a lumen, the lumen configured to slidably receive the first elongated shaft therethrough, wherein the second shaft has a proximal portion configured to be coupled to an energy source and a distal portion configured to be positioned at or adjacent a treatment site within the body lumen;
   - a conductive element carried by the distal portion of the second shaft and configured to be electrically coupled to the energy source to deliver an electrical stimulus to nerves proximate the body lumen at the treatment site; and
   - a therapeutic region at the distal portion of the second shaft, the therapeutic region containing a therapeutic agent configured to prevent or reduce colonization of the substance by a pathogen,
   - wherein, when the distal portion of the second elongated shaft is positioned at or adjacent the treatment site, the therapeutic region is positioned at or near an anatomical location prone to collecting substances containing opportunistic pathogens.
2. The device of Clause 1, wherein the body lumen is a pharynx of the patient.

3. The device of Clause 1 or Clause 2, wherein the anatomical location is a pharyngeal recess of the patient.
4. The device of any one of Clauses 1 to 3, wherein the therapeutic region is configured to release the therapeutic agent when the therapeutic region is in mechanical or fluidic contact with the substances.
5. The device of any one of Clauses 1 to 4, wherein, when the therapeutic region is not in mechanical or fluidic contact with the substances, the therapeutic region does not release the therapeutic agent.
6. The device of any one of Clauses 1 to 5, wherein the therapeutic is configured to release the therapeutic agent for no less than 7 days.
7. The device of any one of Clauses 1 to 6, wherein the therapeutic region comprises a portion of the surface of the second shaft that is impregnated with the therapeutic agent.
8. The device of any one of Clauses 1 to 7, wherein the therapeutic region comprises a coated portion of the second shaft.
9. The device of any one of Clauses 1 to 8, wherein the therapeutic region comprises a therapeutic member positioned on an outer surface of the second shaft.
10. The device of any one of Clauses 1 to 9, wherein a length of the therapeutic region is less than a total length of the second shaft.
11. The device of any one of Clauses 1 to 10, wherein the therapeutic region is a first therapeutic region and the device further comprises a second therapeutic region spaced apart from the first therapeutic region along a longitudinal axis of the second shaft.
12. The device of any one of Clauses 1 to 11, wherein the therapeutic agent comprises antibacterial, antiviral, antifungal, and/or antiprotozoal properties.
13. The device of any one of Clauses 1 to 12, wherein the therapeutic region comprises a metal.
14. The device of any one of Clauses 1 to 13, wherein the substances are a pooled secretion.
15. A device for delivering an electrical stimulus to nerves proximate a body lumen of a human patient and preventing or reducing aspiration of a substance from the body lumen into an airway of the patient, the device comprising:

a first elongated shaft;

a second elongated shaft having a proximal portion configured to be electrically coupled to an energy source and fluidically coupled to a pressure source and a distal portion configured to be positioned at or adjacent a treatment site within the body lumen, the second elongated shaft having a sidewall defining a first lumen configured to slidably receive the first elongated shaft therethrough, a second lumen, and an aperture extending radially between the second lumen and an outer surface of the second elongated shaft; and a conductive element carried by the distal portion of the second elongated shaft and configured to be electrically coupled to the energy source to deliver an electrical stimulus to nerves proximate the body lumen at the treatment site, wherein, when the first and second elongated shafts are positioned in the body lumen with the conductive element located at or adjacent the treatment site, the aperture is located within a treatment distance of a substance within the body lumen, and wherein the pressure source is configured to generate pressure within the second lumen to transport a fluid between the aperture and the pressure source through the second lumen.

16. The device of Clause 15, wherein the pressure source is configured to generate negative pressure within the second lumen to draw the substance into the aperture and proximally through the second lumen.
17. The device of Clause 15 or Clause 16, wherein the pressure source is configured to generate positive pressure within the second lumen to transport a fluid including a therapeutic agent distally through the second lumen and the aperture to the substance.
18. The device of any one of Clauses 15 to 17, wherein the therapeutic agent is an antimicrobial agent configured to prevent or inhibit colonization of the substance by a pathogen.
19. The device of any one of Clauses 15 to 18, wherein the aperture is a first aperture, the device further comprising a second aperture longitudinally spaced apart from the first aperture, the second aperture being fluidically coupled to the second lumen.
20. The device of any one of Clauses 15 to 19, wherein the aperture is a first aperture, the device further comprising a second aperture, the second aperture being fluidically coupled to a third lumen.
21. The device of Clause 20, wherein the second aperture is longitudinally and/or circumferentially spaced apart from the first aperture.
22. The device of any one of Clauses 15 to 21, wherein the body lumen comprises a pharynx of the patient.
23. The device of any one of Clauses 15 to 22, wherein the substance is positioned within a recess of the patient's pharynx.
24. A method of preventing or inhibiting colonization of a substance within a pharynx of a patient by a pathogen, the method comprising:

positioning a device within a pharynx of a patient such that a conductive element carried by the device is positioned at or adjacent a treatment site within the patient's pharynx and a therapeutic agent carried by the device is positioned within a treatment distance of a substance within the patient's pharynx;

stimulating nerves proximate the treatment site via the conductive element; and delivering the therapeutic agent to the substance, wherein the therapeutic agent is configured to prevent or inhibit colonization of the substance by a pathogen.

25. The method of Clause 24, wherein delivering the therapeutic agent comprises releasing the therapeutic agent from the device.
26. The method of Clause 24 or Clause 25, wherein, when the therapeutic agent is positioned within the treatment distance of the substance, the therapeutic agent is in contact with the substance.
27. The method of any one of Clauses 24 to 26, wherein delivering the therapeutic agent to the substance comprises dissolving at least a portion of a therapeutic element carrying the therapeutic agent, wherein the therapeutic element is disposed on an outer surface of the device.
28. The method of any one of Clauses 24 to 27, wherein delivering the therapeutic agent to the substance comprises generating a positive pressure within a lumen of the device to push a fluid carrying the therapeutic agent distally through the lumen and an opening in a sidewall of the device to the substance.

29. A method of preventing or reducing aspiration of a substance in a pharynx of the patient into an airway of the patient, the substance comprising an opportunistic pathogen, wherein the method comprises:

positioning a device within a pharynx of a patient such that a conductive element carried by the device is positioned at or adjacent a treatment site within the patient's pharynx and an opening extending through a sidewall of the device is positioned within a treatment distance of a substance within the patient's pharynx;

stimulating nerves proximate the treatment site via the conductive element; and generating a pressure within a lumen of the device to draw the substance at the treatment site through the opening and proximally through the lumen.

30. The method of Clause 29, wherein generating a pressure within the lumen of the device comprises generating a negative pressure within the lumen to draw the substance into the opening and proximally through the lumen.

31. A device for delivering an electrical stimulus to nerves proximate a body lumen of a human patient and preventing or reducing aspiration of a substance from the body lumen into an airway of the patient, the device comprising:

an elongated member having a proximal portion configured to be electrically coupled to an energy source and fluidically coupled to a pressure source and a distal portion configured to be positioned at or adjacent a treatment site within the body lumen, the elongated member having a sidewall defining a lumen therethrough and an aperture extending radially between the lumen and an outer surface of the elongated member; and a conductive element carried by the distal portion of the elongated member and configured to be electrically coupled to the energy source to deliver an electrical stimulus to nerves proximate the body lumen at the treatment site, wherein, when the elongated member is positioned in the body lumen with the conductive element located at or adjacent the treatment site, the aperture is located within a treatment distance of a substance within the body lumen, and wherein the pressure source is configured to generate pressure within the lumen to transport a fluid between the aperture and the pressure source through the lumen.

32. The device of Clause 31, wherein the elongated member comprises a closed distal end.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

I. Anatomy and Physiology

Figure 1:
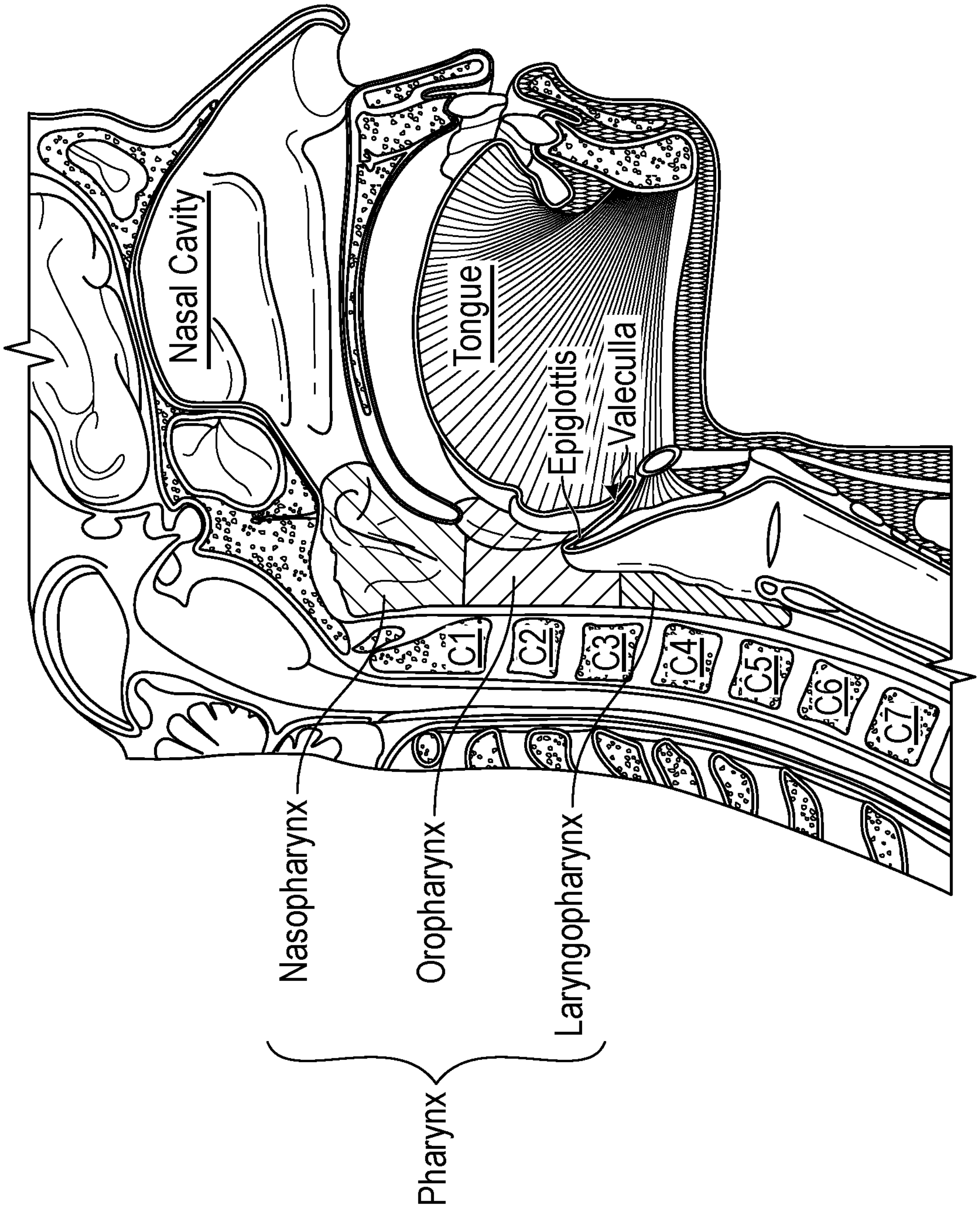
FIG. 1 is a fragmentary sagittal view of a pharynx of a human patient.

The pharynx is the part of the digestive system situated posterior to the nasal and oral cavities and posterior to the larynx. It is therefore divisible into nasal, oral, and laryngeal parts: the (1) nasopharynx, (2) oropharynx, and (3) laryngopharynx. With reference to FIG. 1, the pharynx extends from the base of the skull down to the inferior border of the cricoid cartilage (around the C6 vertebral level), where it becomes continuous with the esophagus. Its superior aspect is related to the sphenoid and occipital bones and the posterior aspect to the prevertebral fascia and muscles as well as the upper six cervical vertebrae. The pharynx is a fibromuscular tube lined by mucous membrane.

The pharynx is the common channel for deglutition (swallowing) and respiration, and the food and air pathways cross each other in the pharynx. In the anesthetized patient, the passage of air through the pharynx is facilitated by extension of the neck.

The nasopharynx, at least in its anterior part, may be regarded as the posterior portion of the nasal cavity, with which it has a common function as part of the respiratory system. The nasopharynx communicates with the oropharynx through the pharyngeal isthmus, which is bounded by the soft palate, the palatopharyngeal arches, and the posterior wall of the pharynx. The isthmus is closed by muscular action during swallowing. The choanae are the junction between nasopharynx and the nasal cavity proper.

A mass of lymphoid tissue, the nasopharyngeal tonsil is embedded in the mucous membrane of the posterior wall of the nasopharynx. Enlarged nasopharyngeal tonsils are termed "adenoids" and may cause respiratory obstruction. Higher up, a minute pharyngeal hypophysis (resembling the adenohypophysis) may be found.

The oropharynx extends inferiorward from the soft palate to the superior border of the epiglottis. It communicates anteriorly with the oral cavity by the faucial (oropharyngeal) isthmus, which is bounded superiorly by the soft palate, laterally by the palatoglossal arches, and inferiorly by the tongue. This area is characterized by a lymphatic ring composed of the nasopharyngeal, tubal, palatine, and lingual tonsils.

The mucous membrane of the epiglottis is reflected onto the base of the tongue and onto the lateral wall of the pharynx. The space on each side of the median glosso-epiglottic fold is termed the epiglottic vallecula.

The laryngopharynx extends from the superior border of the epiglottis to the inferior border of the cricoid cartilage, where it becomes continuous with the esophagus. Its anterior aspect has the inlet of the larynx and the posterior aspects of the arytenoid and cricoid cartilages. The pyriform sinus, in which foreign bodies may become lodged, is the part of the cavity of the laryngopharynx situated on each side of the inlet of the larynx.

A. Muscles

The pharynx consists of four coats of muscles, from within outward: (1) a mucous membrane continuous with that of the auditory tubes and the nasal, oral, and laryngeal cavities; (2) a fibrous coat, that is thickest in its superior extent (pharyngobasilar fascia) and that forms a median raphe posteriorly; (3) a muscular coat, described below; and (4) a fascial coat (buccopharyngeal fascia) covering the outer surface of the muscles.

The wall of the pharynx is composed mainly of two layers of skeletal muscles. The external, circular layer comprises three constrictors. The internal, chiefly longitudinal layer consists of two levators: the stylopharyngeus and the palatopharyngeus.

The chief action in which the muscles of the pharynx combine is deglutition (or swallowing), a complicated, neuromuscular act whereby food is transferred from (1) the mouth through (2) the pharynx and (3) the esophagus to the stomach. The pharyngeal stage is the most rapid and most complex phase of deglutition. During swallowing, the nasopharynx and vestibule of the larynx are sealed but the epiglottis adopts a variable position. Food is usually deviated laterally by the epiglottis and ary-epiglottic folds into the piriform recesses of the laryngopharynx, lateral to the larynx. The pharyngeal ridge is an elevation or bar on the posterior wall of the pharynx inferior to the level of the soft palate; it is produced during swallowing by transverse muscle fibers.

B. Innervation and Blood Supply

The motor and most of the sensory supply to the pharynx is by way of the pharyngeal plexus, which is formed by the pharyngeal branches of the vagus and glossopharyngeal nerves and also by sympathetic nerve fibers. The motor fibers in the plexus are carried by the vagus (although they likely represent cranial accessory nerve components) and supply all the muscles of the pharynx and soft palate except the stylopharyngeus (supplied by cranial nerve IX) and tensor veli palatini (supplied by cranial nerve V). The sensory fibers in the plexus are from the glossopharyngeal nerve, and they supply the greater portion of all three parts of the pharynx. The pharynx is supplied by branches of the external carotid (ascending pharyngeal) and subclavian (inferior thyroid) arteries.

II. System Overview

Figure 2:
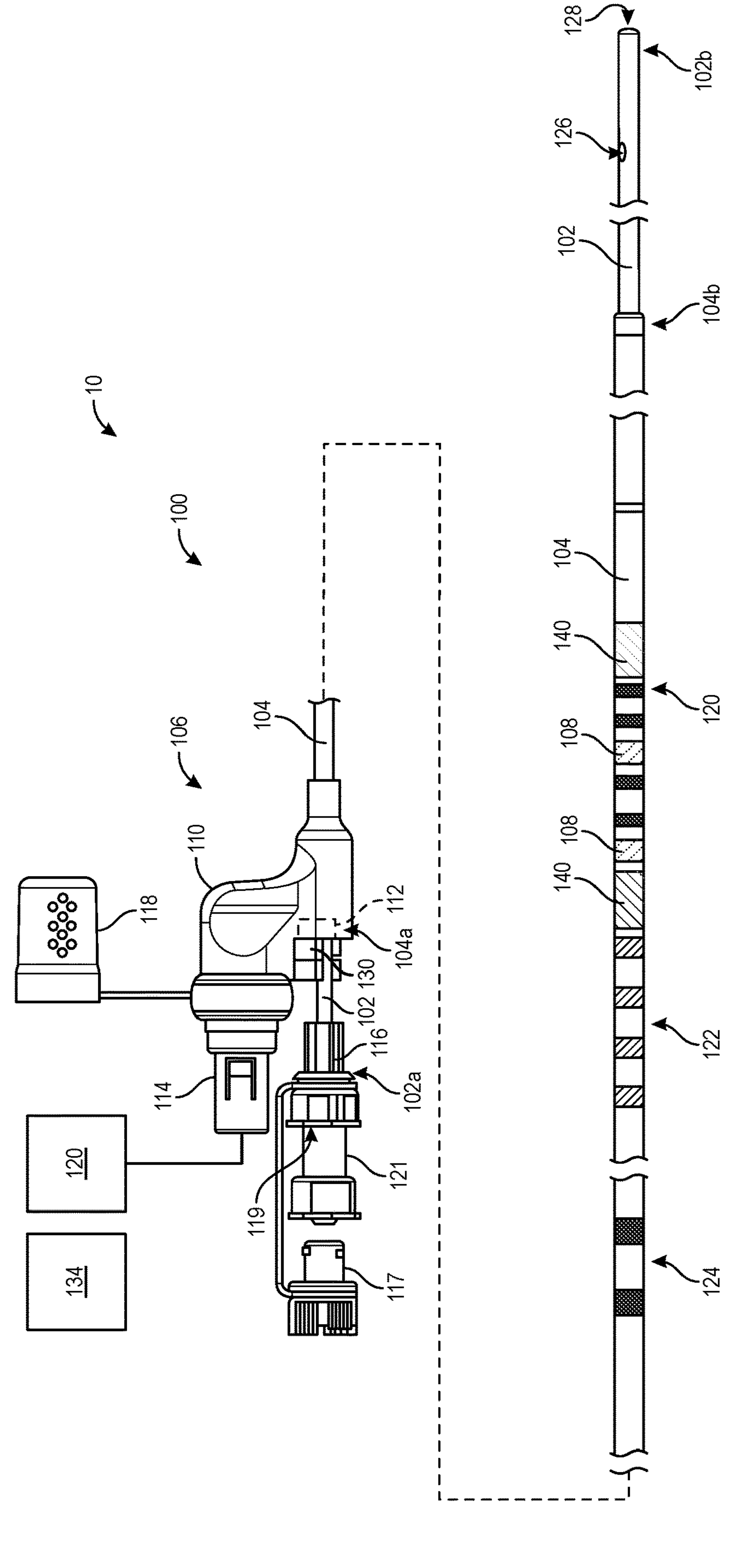
FIG. 2 depicts an electrical stimulation device in accordance with several embodiments of the present technology.
Figure 3A:
FIG. 3A is a fragmentary sagittal view of an electrical stimulation device transnasally inserted into a pharynx of a patient in accordance with several embodiments of the present technology.
Figure 3B:
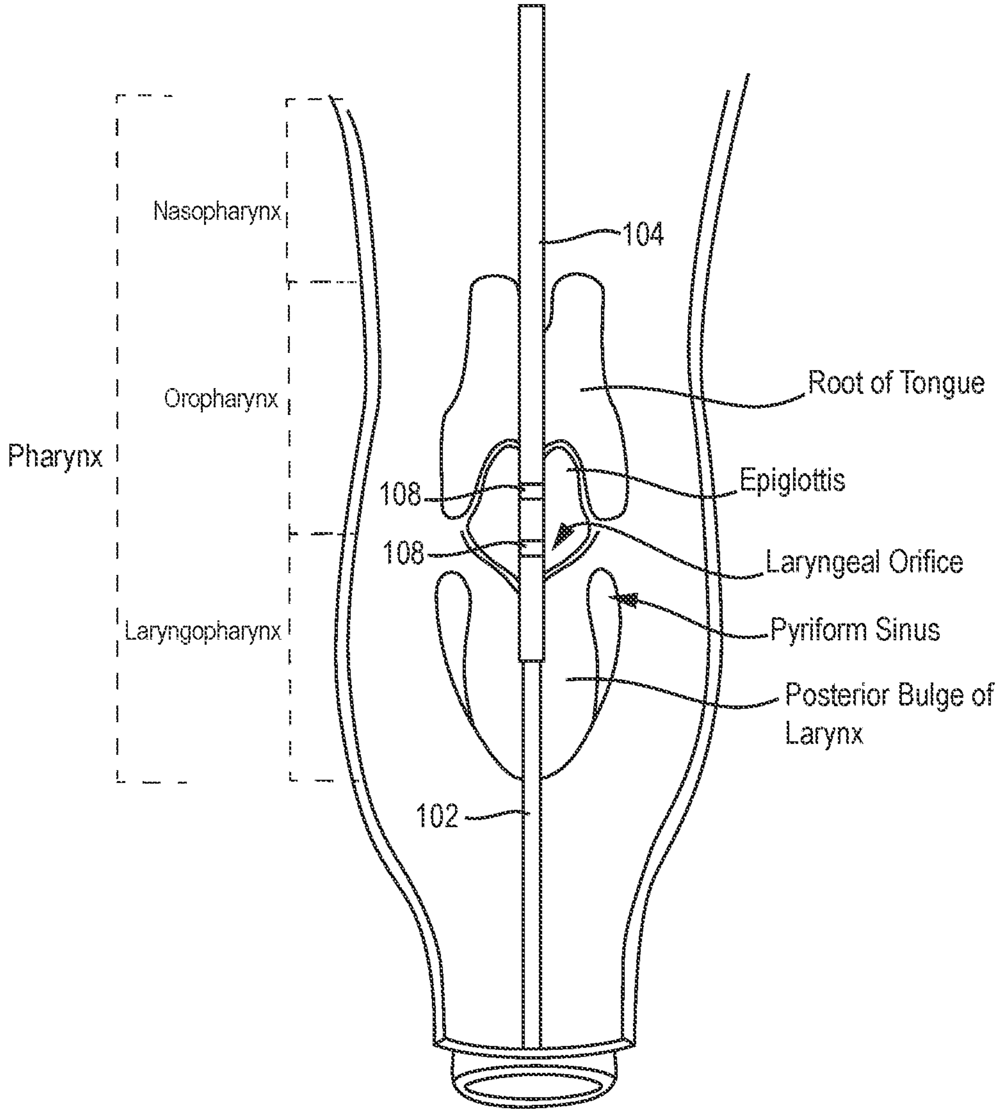
FIG. 3B is an open posterior view of an electrical stimulation device transnasally inserted into a pharynx of a patient in accordance with several embodiments of the present technology.

FIG. 2 depicts a treatment system 10 configured in accordance with several embodiments of the present technology. The system 10 may comprise a device 100 configured to provide intraluminal electrical stimulation to a patient suffering from a medical condition, and a current generator 120 configured to be electrically coupled to the device 100. The device 100 can include a handle assembly 106, a first elongated shaft 102 (or "first shaft 102"), and a second elongated shaft 104 (or "second shaft 104") configured to slidably receive the first shaft 102 therethrough. The first shaft 102 can be a flexible tube configured to deliver nutrients to the patient. For example, in some embodiments the first shaft 102 comprises a nasogastric feeding tube. Each of the first and second shafts 102, 104 have a proximal portion 102*a* and 104*a*, respectively, coupled to the handle assembly 106, and a distal portion 102*b* and 104*b*, respectively, configured to be positioned within an upper gastrointestinal tract of the patient. As depicted in FIGS. 3A and 3B, when the device 100 is inserted into the patient, the distal portion 102*b* of the first shaft 102 is configured to be positioned within the patient's stomach, and the distal portion 104*b* of the second shaft 104 is configured to be positioned at a treatment site within the patient's pharynx. The device 100 further includes one or more conductive elements 108 carried by the distal portion 104*b* of the second shaft 104 and configured to deliver stimulation energy to nerves proximate the treatment site.

As shown in FIG. 2, the handle assembly 106 can include a hub 110 and one or more connectors and/or accessory components configured to be removably coupled to the hub 110. The hub 110 can include a housing having a first portion fixedly coupled to the proximal portion 104*a* of the second shaft 104, and a second portion configured to house one or more electrical components. In some embodiments, the second portion of the housing is positioned laterally of the first portion of the housing. The hub 110 may further include an electrical connector 114 at the second portion that provides an electrical interface between the second shaft 104 and the current generator 120.

In some embodiments, the device 100 includes a connector 116 coupled to the proximal portion 102*a* of the first shaft 102 and having one or more ports, such as port 119, configured to be coupled to one or more accessory devices or systems. For example, the port 119 may be configured to be releasably coupled to an enteral feeding set (not shown) for delivering nutrients through the first elongated shaft 102 into the patient's stomach. Additionally or alternatively, the port 119 can be configured to be releasably coupled to a guidewire assembly. For example, the port 119 can be configured to receive a guidewire (not visible) therethrough to assist with inserting the device 100 into the patient. The guidewire assembly can include a guidewire grip 121 coupled to the proximal end portion of the guidewire. In some embodiments, the connector 116 includes one or more additional ports, such as a port configured to be fluidly coupled to a syringe or other fluid source and/or pressure source. The connector 116 may further comprise a cap 117 tethered to the connector 116 and configured to be secured over the port 119 when not in use.

As previously mentioned, the first shaft 102 is configured to be inserted through a lumen of the second shaft 104. In use, the distal portion 102*b* of the first shaft 102 can be inserted into an opening at the proximal portion 104*a* of the second shaft 104 that is fixed to the hub 110. In some embodiments, the device 100 includes a sealing member (not visible) at the hub 110 that engages the first and second shafts 102, 104 to prevent fluid from within a patient being drawn up within a space between the first and second shafts 102, 104 by way of capillary action when the second shaft 104 is removed from the patient. The sealing member may also be configured to clean any matter off of the first shaft 102 as it is withdrawn from the patient.

The first shaft 102 can have an atraumatic distal tip for patient comfort and ease of inserting the first shaft 102 into the patient. The first shaft 102 can have an opening 128 at its distal end and/or one or more apertures 126 extending through the sidewall along the distal portion 102*b* of the first shaft 102. Nutrients can be dispersed from the first shaft 102 into the patient's stomach via the one or more apertures 126 and/or the opening 128.

Each of the conductive elements 108 may comprise an electrode, an exposed portion of a conductive material, a printed conductive material, and other suitable forms. In some embodiments, for example as shown in FIG. 2, the conductive elements 108 comprise a pair of ring electrodes configured to deliver bipolar stimulation energy. The conductive elements 108 can be crimped, welded, or otherwise adhered to an outer surface of the second shaft 104. In some embodiments, the conductive elements 108 comprise a flexible conductive material disposed on the second shaft 104 via printing, thin film deposition, or other suitable techniques. While the device 100 shown in FIG. 2 includes two conductive elements 108, in some embodiments the device 100 may include more or fewer than two conductive elements 108. For example, the device 100 may comprise a single conductive element 108 configured to generate a monopolar electric field. Such embodiments include a neutral or dispersive electrode electrically connected to the current generator 120 and positioned on the patient's skin. In some embodiments, the device 100 may include three or more conductive elements 108 spaced apart along a longitudinal axis of the second shaft 104.

The device 100 may include one or more conductive leads (not visible) extending between a proximal portion of the device 100, such as the hub 110, and the conductive elements 108. In some embodiments, for example, the conductive leads comprise two wires, each extending distally from the hub 110 through a channel (the same channel or different channels) in the second shaft 104 to a corresponding one of the conductive elements 108. The channel(s), for example, can extend longitudinally within a sidewall of the shaft 104. The conductive leads can be insulated along all or a portion of their respective lengths.

In some embodiments, the device 100 is configured such that a position of the second shaft 104 can be fixed relative to a position of the first shaft 102 (or vice versa). The position of the first shaft 102 relative to the second shaft 104 may be adjusted prior to insertion of the device 100 into the patient. Once adjustment is complete, the relative positions of the first shaft 102 and second shaft 104 may be substantially fixed. For example, as shown in FIG. 2, the proximal portion 100*a* of the device 100 can include a retaining structure 130 configured to be coupled to the hub 110 and/or the proximal portions 102*a*, 104*a* of one or both of the second shaft 104 and the first shaft 102. The retaining structure 130 can have a first portion on or through which the second shaft 104 and/or first shaft 102 may be movably or fixedly positioned, and a second portion moveable relative to the first portion. When the second portion is in an open position (as shown in FIG. 2), the first shaft 102 and the second shaft 104 can move longitudinally relative to one another. When the second portion is in a closed position (not shown), the longitudinal and/or radial positions of the first shaft 102 and the second shaft 104 are substantially fixed relative to one another.

The retaining structure 130 may be fixed to one of the first shaft 102 or the second shaft 104 and, at least in the open configuration, allow movement of the other of the first shaft 102 and the second shaft 104. In some embodiments, for example as shown in FIG. 2, the proximal portion of the second shaft 104 is fixed to the retaining structure 130 and the proximal portion of the first shaft 102 is slidably received by the first portion when the device 100 is assembled and the second portion is in an open position. When the second portion is in a closed position, the second portion engages the first shaft 102 and fixes the first shaft 102 relative to the second shaft 104, the hub 110, and/or the retaining structure 130.

In any case, the portion of the retaining structure 130 configured to engage the first and/or second shafts 102, 104 can comprise a high friction thermoplastic elastomer liner that engages the proximal portion of the first shaft 102 when the second portion is in the closed position. The liner can be configured to reduce the compressive force required to fix the first shaft 102 and thereby prevent pinching of the first shaft 102. Other suitable shapes, materials, positions, and configurations for the retaining structure 130 are possible. For example, the retaining structure 130 can comprise one or more magnets, a screw and threaded insert, a radial compression clip, and/or others to fix the proximal portion of the first shaft 102 to the retaining structure 130, the hub 110, and/or the second shaft 104.

As previously mentioned, the proximal portion of the device 100 and/or second shaft 104 is configured to be electrically coupled to a current generator 120 for delivering electric current to the conductive elements 108. The current generator 120, for example, can include a power source and a controller. The controller includes a processor coupled to a memory that stores instructions (e.g., in the form of software, code or program instructions executable by the processor or controller) for causing the power source to deliver electric current according to certain parameters provided by the software, code, etc. The power source of the current generator 120 may include a direct current power supply, an alternating current power supply, and/or a power supply switchable between a direct current and an alternating current. The current generator 120 can include a suitable controller that can be used to control various parameters of the energy output by the power source or generator, such as intensity, amplitude, duration, frequency, duty cycle, and polarity. Instead of or in addition to a controller, the current generator can include drive circuitry. In such embodiments, the current generator can include hardwired circuit elements to provide the desired waveform delivery rather than a software-based generator. The drive circuitry can include, for example, analog circuit elements (e.g., resistors, diodes, switches, etc.) that are configured to cause the power source to deliver electric current according to the desired parameters. For example, the drive circuitry can be configured to cause the power source to deliver periodic waveforms. In some embodiments, the drive circuitry can be configured to cause the power source to deliver a unipolar square wave.

The current generator 120 may be configured to provide a stimulation energy to the conductive elements 108 that has an intensity, amplitude, duration, frequency, duty cycle, and/or polarity such that the conductive elements 108 apply an electric field at the treatment site that promotes neuroplasticity in the areas of the brain associated with swallowing control. Without being bound by theory, it is believed that the treatment energy of the present technology induces and accelerates a cortical reorganization process whereby responsibility for the control and coordination of swallowing activity is moved from the damaged area of the brain to a complementary area of the cortical centers with intact function. The treatment energy of the present technology may also increase local levels of swallow-related neurotransmitters in the pharynx, such as in the oropharynx.

The controller can automatically vary the voltage (to a maximum of 250V) in order to deliver the set current. In some embodiments, the only user adjustable parameter is the stimulation intensity which is derived during treatment level optimization prior to every treatment. Patient specific threshold levels are determined by establishing a sensory threshold followed by measurement of the maximum tolerated stimulation intensity. The controller may automatically calculate the correct stimulation level from the sensory threshold and maximum tolerated stimulation intensity and sets this as the output. The current generator 120 can provide, for example, a current of about 1 mA to about 50 mA, about 1 mA to about 40 mA, about 1 mA to about 30 mA, about 1 mA to about 20 mA, or about 1 mA to about 10 mA, at a frequency of about 1 Hz to about 50 Hz, about 1 Hz to about 40 Hz, about 1 Hz to about 30 Hz, about 1 Hz to about 20 Hz, about 1 Hz to about 10 Hz, about 2 Hz to about 8 Hz, about 1 Hz, about 2 Hz, about 3 Hz, about 4 Hz, about 5 Hz, about 6 Hz, about 7 Hz, about 8 Hz, about 9 Hz, or about 10 Hz, and having a pulse width of about 150 μS to about 250 μS, about 175 μS to about 225 μS, or about 200 μS.

The current generator 120 may also be configured to monitor contact quality between the conductive elements 108 and patient tissue during treatment set up/optimization and throughout the treatment process. In some embodiments, the current generator 120 records and stores patient information and includes a USB port to enable downloading of patient data. The current generator may include a touch screen user interface and software to guide a user through the treatment process.

III. Example Methods of Use

Without being bound by theory, it is believed that increasing peripheral (sensory) feedback to higher brain centers is a key factor to swallowing rehabilitation. As such, the device 100 of the present technology is configured to stimulate sensory nerves associated with swallowing, thereby inducing and accelerating a cortical reorganization process whereby responsibility for the control and coordination of swallowing activity is moved from the damaged area of the brain to a complementary area of the cortical centers of the brain with intact function. It is also believed that the stimulation energy of the present technology can increase local levels of swallow-related neurotransmitters in the pharynx, such as in the oropharynx.

FIGS. 3A and 3B are a fragmentary sagittal view and an open posterior view, respectively, of a patient's throat with a device 100 of the present technology inserted through the patient's nasal cavity into the pharynx. As shown, during a given treatment, the distal portion of the second shaft 104 is positioned at a treatment site in the pharynx with the conductive elements 108 in apposition with the posterior pharyngeal wall. In some embodiments, the conductive elements 108 are positioned within a treatment window along the oropharynx and/or the laryngopharynx. In some embodiments, the conductive elements 108 are positioned at a location along the pharynx that is equivalent to the junction between the C3 and C4 cervical vertebrae. Accordingly, when energy is delivered to the conductive elements 108 by the current generator 120, the conductive elements 108 emit an electric field that flows through the posterior wall of the pharynx, the base of the tongue, the epiglottis, and the region above the larynx. Each of these regions includes a high density of targeted sensory nerves for treating dysphagia, including the pharyngeal plexus, the superior laryngeal branch of the vagus nerve, the lingual branch of the glossopharyngeal nerve, the internal branch of the superior laryngeal nerve, and/or the external branch of the superior laryngeal nerve.

In some embodiments, the first and/or second shafts 102, 104 can comprise one or more indicators (such as indicators 120, 122, and 124 in FIG. 2) configured to facilitate insertion and positioning of the device 100 within the patient. For example, the indicator can comprise one or more visual markings that, when viewed through the patient's oral cavity, indicate the conductive elements 108 are properly positioned or that the second shaft 104 (and/or conductive elements 108) should be inserted further or withdrawn. In some embodiments, the indicator comprises one or more circumferential markings (such as one or more colored bands) printed on the second shaft 104.

When the conductive elements 108 are in a desired position, stimulation energy is delivered to the treatment site. In some embodiments, the delivered current is a unipolar square wave having an amplitude between 1 mA and 50 mA, a frequency of 5 Hz, and a pulse duration of 200 μS. Each treatment session can have a duration between 5 minutes and 20 minutes. For example, the treatment session can have a duration of 10 minutes. In some embodiments, a patient can undergo a single treatment per day over the course of multiple days of treatment. For example, a patient can undergo one treatment session per day for three to six consecutive days. In some embodiments, the patient may undergo multiple treatment sessions per day and/or per week. Still, other current parameters and treatment parameters are possible.

In some embodiments, the device 100 does not include the first elongated shaft 102. In such embodiments, the device 100 may only include the second elongated shaft 104. For example, the device 100 may comprise a stimulation device comprising an elongated member having one or more lumens extending therethrough and does not include a feeding tube. For example, the one or more lumens may be used for transporting a fluid as described herein with reference to FIGS. 4A-6.

IV. Devices Configured to Prevent or Reduce Aspiration of Pharyngeal Substances

While the etiology of aspiration pneumonia is multifactorial, there is a strong association between dysphagia and the development of aspiration pneumonia. Routine clearance of secretions, an intact cough reflex, and adequate expiratory pressure are usually adequate defenses against aspiration (entry of material into the airway below the level of the true vocal cords). Approximately half of all healthy adults aspirate small amounts of oropharyngeal secretions during sleep. The low virulent bacterial burden of normal pharyngeal secretions, together with forceful coughing, active ciliary transport, and normal humoral and cellular immune mechanisms result in clearance of the inoculum without sequelae. In dysphagic patients, however, poor oral hygiene is common and normal microbial flora are often replaced by opportunistic pathogens. Moreover, there is frequently pooling of secretions in the pharyngeal recesses (e.g., the valleculae, the pyriform sinuses) due to an absent swallow, a missing or weak cough reflex, and discoordination of the airway closure mechanisms. Collectively these conditions can result in aspiration of the pooled secretions into the airways and subsequent infection.

The present technology may be configured to treat a pharyngeal substance to reduce a patient's risk of developing aspiration pneumonia. As used herein, "treating" or "treatment of" a pharyngeal substance refers to preventing and/or inhibiting colonization of a pharyngeal substance by one or more pathogens, reducing an amount of the pharyngeal substance in the pharynx, and/or removing the pharyngeal substance from the pharynx. As used herein, the term "pathogen" refers to a primary pathogen and/or an opportunistic pathogen. A pharyngeal substance may include saliva, mucous, food residue, an ingested liquid, a physiologic fluid, and/or combinations thereof. Moreover, a "pooled" pharyngeal substance can refer one or more pharyngeal substances that have collected in a certain location within the patient's pharynx. For example, a pooled pharyngeal substance can be located in a pharyngeal recess (e.g., vallecula, pyriform sinus), on a wall of the pharynx, and/or at a base of the patient's tongue. Treatment of a "pooled" pharyngeal substance can mean treating a pharyngeal substance while it remains pooled in the collection location, or can mean treating a pharyngeal substance that had once been pooled but at the time of treatment has been displaced (e.g., by the dynamic environment of the throat, by interaction with the stimulation device or another device, etc.).

In some embodiments, a device of the present technology is configured to locally deliver a therapeutic agent to the pharyngeal substance. The therapeutic agent can be configured to prevent and/or inhibit colonization of the pharyngeal substance by a pathogen so that if a patient aspirates the pharyngeal substance there is a lower risk of infection. For example, a portion of the device can carry the therapeutic agent such that, when the device is inserted into the patient's pharynx, the portion of the device carrying the therapeutic agent is positioned within the patient's pharynx and releases the therapeutic agent at or near the pharyngeal substance. In some embodiments, the device is configured to selectively release the therapeutic agent. For example, the device may be configured to only release the therapeutic agent when the therapeutic agent is in contact with the pharyngeal substance. In some embodiments, an amount of the therapeutic agent released can depend on a degree of pooling of the pharyngeal substance (e.g., a larger pooled pharyngeal substance will cause the device to release a greater amount of the therapeutic agent). Accordingly, the device can be configured to release the therapeutic agent to the locations with the greatest risk of pathogen colonization and with low unproductive release of the therapeutic agent. Such controlled release enables a high concentration of the therapeutic agent to be delivered over an extended period of time with reduced risk of clinical complications. In some embodiments, the therapeutic agent is disposed on or impregnated within a portion of the device. In some embodiments, the device is configured to deliver a fluid carrying a therapeutic agent directly to a pharyngeal substance via a lumen and sidewall opening in the device. Alternatively or additionally, the device can be configured to draw a pharyngeal substance into and proximally through a lumen of the device to remove the pharyngeal substance from the patient's pharynx.

In some embodiments, for example as shown in FIG. 2, the second shaft 104 comprises a therapeutic region 140 disposed at or along one or more portions of the second shaft 104. The therapeutic region 140 may comprise a therapeutic agent. As shown in FIG. 2, each therapeutic region 140 of the second elongated shaft 104 can have a length less than a total length of the second shaft 104. Although FIG. 2 depicts two therapeutic regions 140 along the second shaft 104, the second shaft 104 can carry any suitable number therapeutic regions 140. For example, the therapeutic region 140 can be disposed at multiple portions of the second shaft 104, each therapeutic region 140 having a length less than a total length of the second shaft 104 and longitudinally spaced apart from the other therapeutic regions 140. In some embodiments, the therapeutic region 140 can be disposed along a single, continuous portion of the second shaft 104.

Figure 4A:
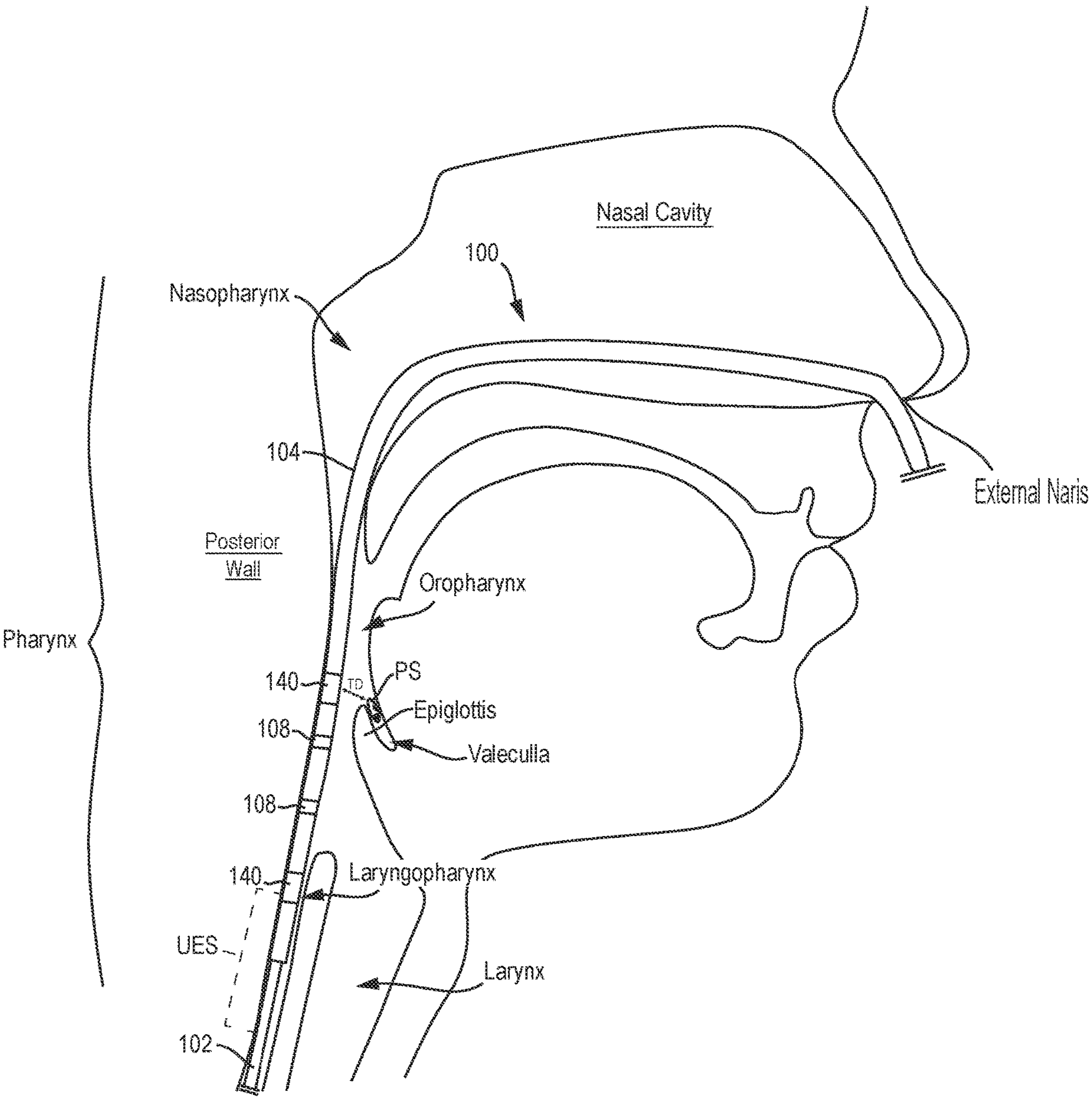
FIGS. 4A-4C depict an electrical stimulation device transnasally inserted into a pharynx of a patient in accordance with several embodiments of the present technology.
Figure 4B:
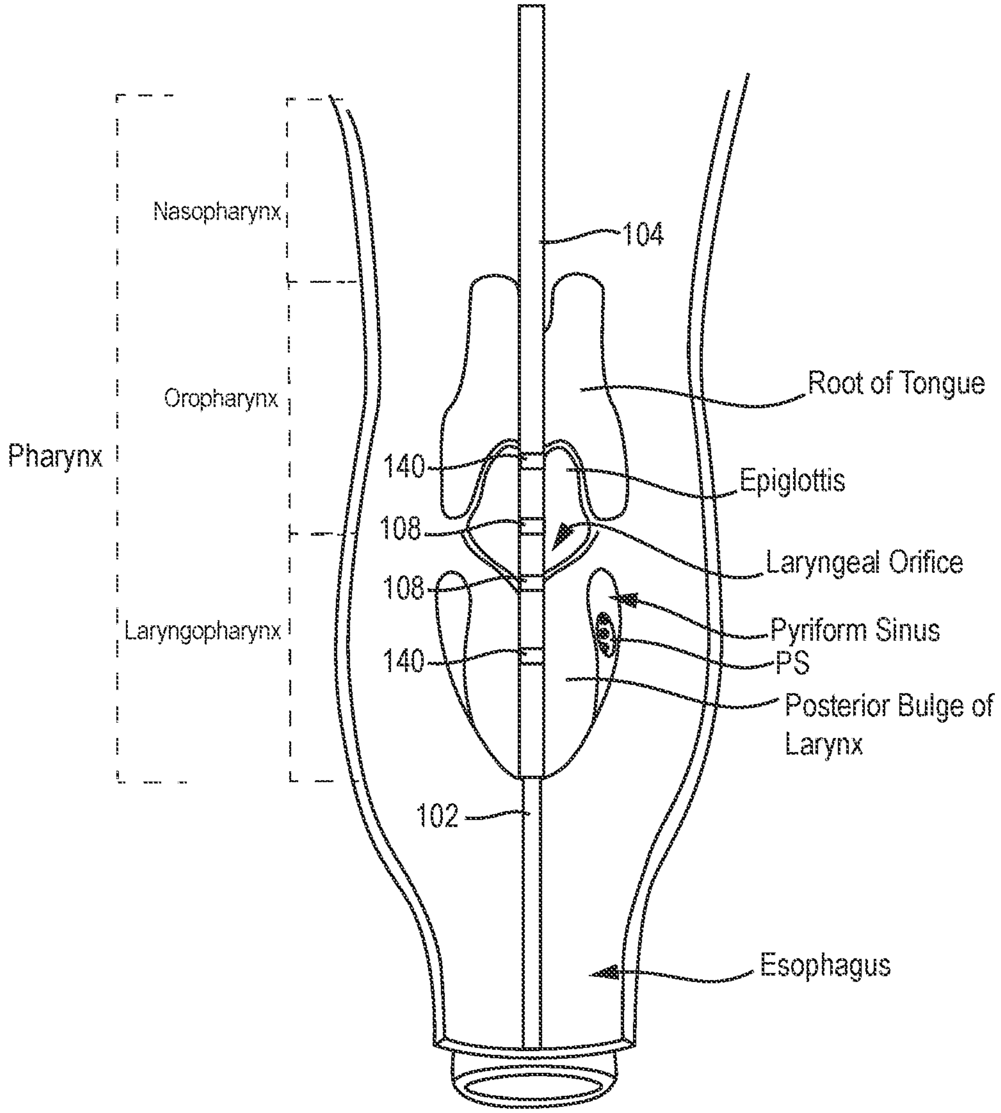
Figure 4C:
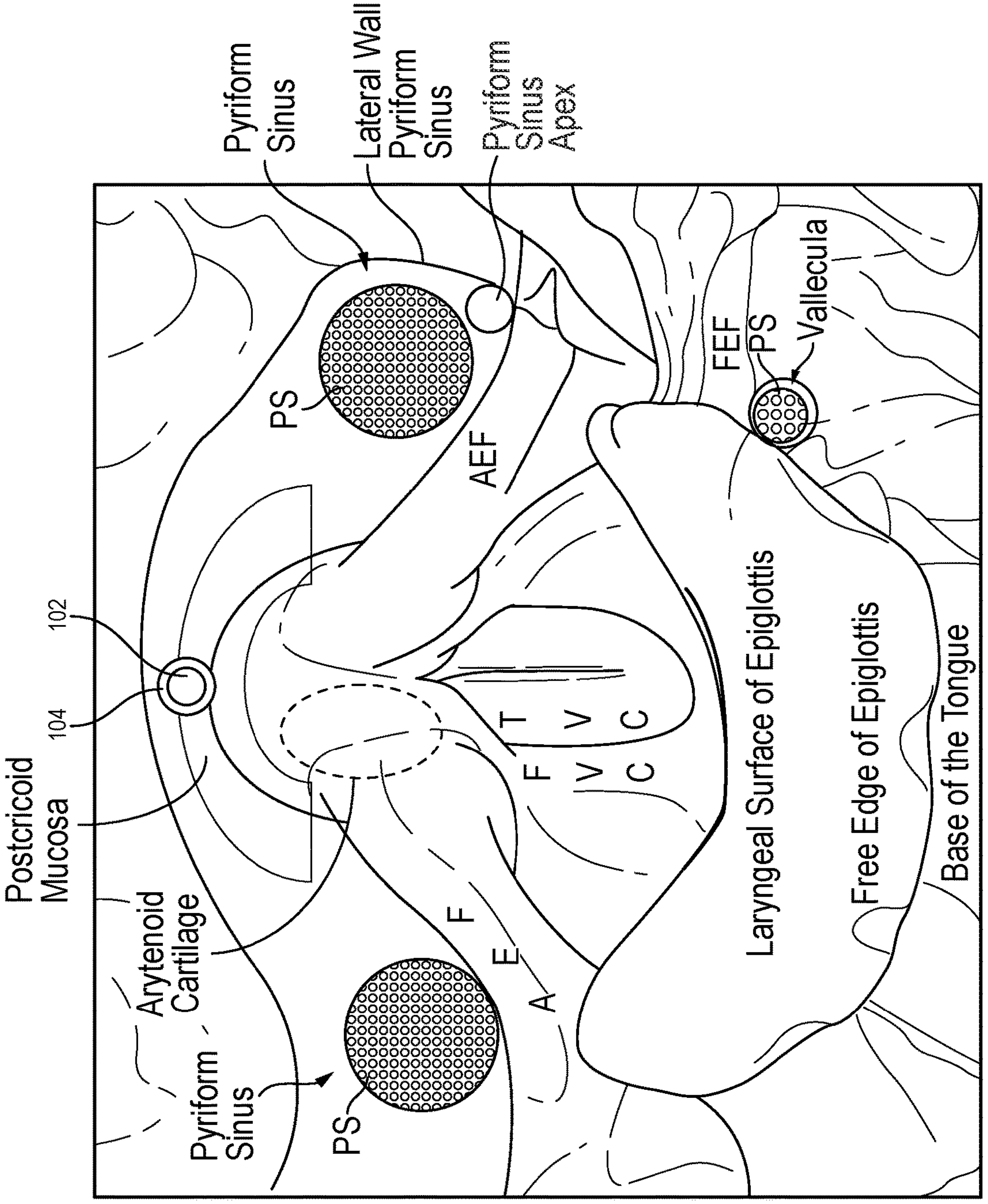

The therapeutic region 140 can be positioned distal of the conductive elements 108 (see FIG. 2), proximal of the conductive elements 108 (see FIG. 2), and/or between the conductive elements 108. In some embodiments, the therapeutic element is positioned between the distal end of the second shaft 104 and a most proximal oral indicator 122. The position of the therapeutic region 140 along the second shaft 104 can be based, at least in part, on a common anatomical location for pooled pharyngeal substances. For example, as shown in FIGS. 4A-4C, when the device 100 is inserted into the patient's pharynx and the conductive elements 108 are positioned at or adjacent a treatment site to be electrically stimulated, the portions of the second shaft 104 carrying the therapeutic agent can be positioned within a treatment distance TD of a pharyngeal substance PS such that the therapeutic region 140 and/or agent can interact (e.g., mechanically, fluidically, chemically, etc.) with the pharyngeal substance PS. In some embodiments, when the therapeutic region 140 is positioned within the treatment distance TD of the pharyngeal substance PS, the therapeutic region 140 is positioned at or adjacent a location of the pharyngeal substance PS. For example, a first portion of the second shaft 104 carrying the therapeutic region 140 and/or agent can be positioned at or adjacent the patient's vallecula (see FIG. 4A) and a second portion of the second shaft 104 carrying the therapeutic region 140 and/or agent can be positioned at or adjacent the patient's pyriform sinuses (see FIG. 4B). In some embodiments, when the therapeutic region 140 is positioned within the treatment distance TD of the pharyngeal substance PS, the therapeutic region 140 is positioned in contact with the pharyngeal substance PS. In some embodiments, when the device 100 is inserted into the patient's pharynx, the therapeutic region(s) 140 can be positioned proximal of a pharyngeal substance PS. For example, the portion of the second shaft 104 carrying the therapeutic region 140 and/or agent can be configured to be positioned within a patient's nasal cavity, nasal pharynx, oropharynx, etc.

The therapeutic agent may be any substance (or combination of substances) that provides a therapeutic effect in a patient in need thereof. In some embodiments, the therapeutic agent is an antimicrobial agent and/or an antibiotic agent and is configured to prevent and/or inhibit colonization of the pharyngeal substance by a pathogen. The therapeutic agent can have antibacterial, antiviral, fungicidal, and/or antiprotozoal properties. The therapeutic agent can be microbicidal (e.g., configured to kill pathogens) and/or biostatic (e.g., configured to inhibit pathogen growth). In some embodiments, the therapeutic agent can comprise a metal or metal alloy (e.g., silver, copper, zinc, etc.). Examples of suitable antibiotics and antimicrobials include, but are not limited to, amoxicillin, amoxicillin/clavulanate, cephalexin, ciprofloxacin, clindamycin, metronidazole, azithromycin, levofloxacin, sulfamethoxazole/trimethoprim, tetracycline(s), minocycline, tigecycline, doxycycline, rifampin, triclosan, chlorhexidine, penicillin(s), aminoglycides, quinolones, fluoroquinolones, vancomycin, gentamycin, cephalosporin(s), carbapenems, imipenem, ertapenem, antimicrobial peptides, cecropin-mellitin, magainin, dermaseptin, cathelicidin, α-defensins, and α-protegrins.

In some embodiments, the therapeutic region 140 comprises a portion of the sidewall of the second shaft 104 that has been impregnated with a therapeutic agent. For example, the sidewall of the second shaft 104 can be impregnated with silver nanoparticles. Additionally or alternatively, the therapeutic agent can be disposed on an outer surface of the second shaft 104 via covalent bonding, physical adsorption, surface initiated immobilization, and/or other suitable methods. For example, silver can be deposited on the outer surface of the second shaft 104 via ion beam deposition. The therapeutic region can extend completely or partially around a circumference of the second shaft 104.

In some embodiments, the device 100 can include one or more therapeutic members disposed on the outer surface of the second shaft 104. The therapeutic member can contain a therapeutic agent. The therapeutic member can comprise, but is not limited to, a coating, a film, a sheet, a strip, a ribbon, a capsule, a matrix, a wafter, a pellet, or other pharmaceutical delivery apparatus or a combination thereof.

The therapeutic element can be adhered to, coupled to, deposited on, monolithic with, or otherwise joined to an outer surface of the second shaft 104.

The therapeutic agent can be configured to be selectively released from the second shaft 104 and/or therapeutic member in a controlled manner. In some embodiments, the therapeutic agent is configured to be released only when the therapeutic agent is positioned within the treatment distance TD of the pharyngeal substance PS. For example, release of the therapeutic agent can be initiated when the therapeutic member and/or therapeutic region 140 is positioned in fluidic contact with the pharyngeal substance PS. In some embodiments, the therapeutic region 140 and/or member comprises one or more control features configured to regulate the release of the therapeutic agent. For example, the therapeutic member and/or region 140 can comprise a biodegradable coating that does not include the therapeutic agent so that the therapeutic agent is not released until the biodegradable coating has degraded.

As pooling of pharyngeal substances in the patient's pharynx can occur continuously and over an extended period, the therapeutic region 140 and/or member can be configured to release the therapeutic agent over a desired period of time. For example, the desired period of time can be at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, or at least 30 days. In some embodiments, the therapeutic region 140 can be configured to release the therapeutic agent in a selective manner (e.g., only when the therapeutic region 140 is in contact with the pharyngeal substance PS). In some embodiments, the therapeutic region 140 can be configured to release the therapeutic agent in a continuous manner at a constant rate and/or a rate based, at least in part, on a condition of the environment surrounding the therapeutic region 140 (e.g., contact with the pharyngeal substance PS, a humidity of the environment, a temperature of the environment, etc.).

The therapeutic agent carried by the therapeutic region 140 and/or the second shaft 104 may be highly concentrated. By containing the therapeutic region 140 and/or agent to discrete portions of the second shaft 104 and by releasing the therapeutic agent directly to the pharyngeal substance PS, a strong dose of the therapeutic agent can be delivered with low risk of subsequent clinical complications. In some embodiments, the therapeutic region 140 and/or member comprises a low payload of the therapeutic agent. As the therapeutic element may be configured to release the therapeutic agent in a controlled manner (e.g., when in the presence of a pharyngeal substance PS), a lower total dose of the therapeutic agent may be required over the course of treatment.

Figure 5:
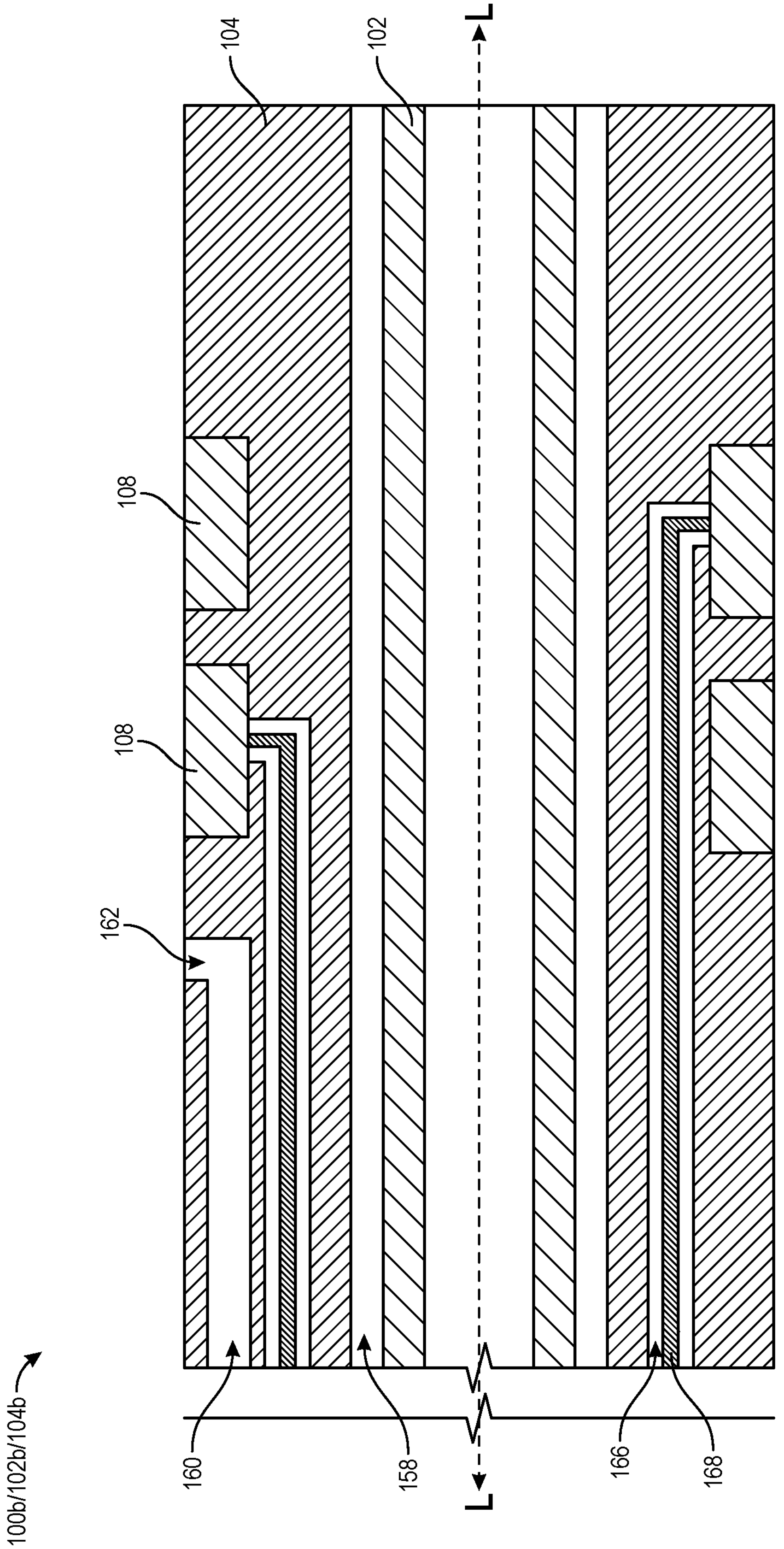
FIG. 5 is a cross-sectional schematic view of an electrical stimulation device in accordance with several embodiments of the present technology.
Figure 6:
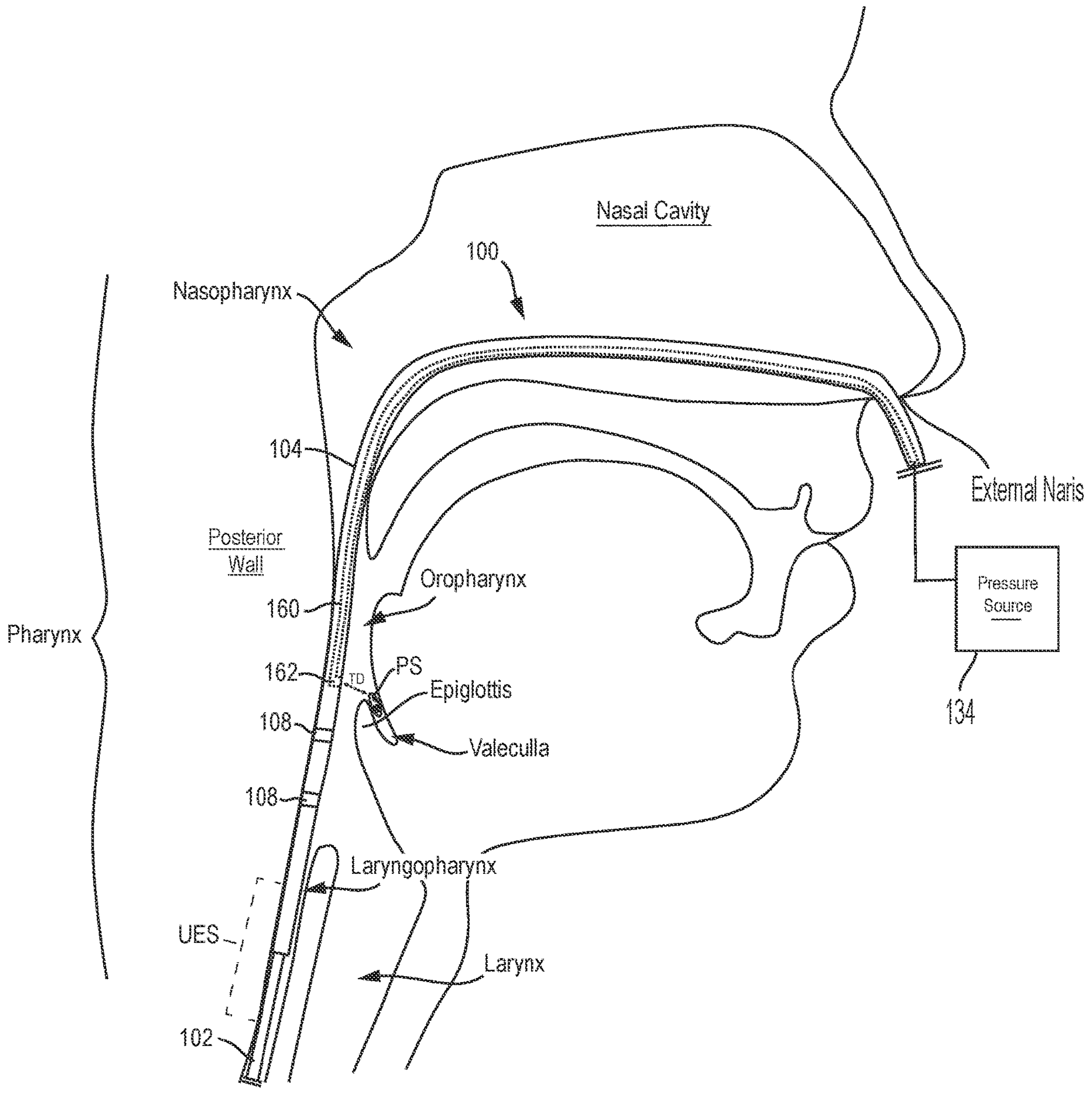
FIG. 6 depicts an electrical stimulation device transnasally inserted into a pharynx of a patient in accordance with several embodiments of the present technology.

FIGS. 5 and 6 depict a device 100 in accordance with the present technology configured to treat pooled secretions by having one or more drug delivery and/or aspiration ports. FIG. 5 is a cross-sectional view of the distal end 100*b* of the device 100 and FIG. 6 shows the device 100 inserted into the patient's pharynx. As shown in FIG. 5, the second shaft 104 can define a first lumen 158 extending along a longitudinal axis L of the device 100. The first lumen 158 can be configured to receive the first elongated shaft 102 therethrough. As shown in FIGS. 5 and 6, the second shaft 104 can define a second lumen 160 extending along the longitudinal axis L and positioned radially adjacent to the first lumen 158. The second lumen 160 can have a proximal end portion configured to be fluidically coupled to a pressure source 134. The pressure source 134 can be a pump such as a rotary vane pump, a centrifugal pump, a screw pump, a peristaltic pump, an impeller pump, a roller pump, or others. A distal end portion of the second lumen 160 can be configured to be fluidically coupled to an aperture 162 extending radially between the second lumen 160 and an outer surface of the second shaft 104. The aperture 162 can be positioned distal of the conductive elements 108, between the conductive elements 108, and/or proximal of the conductive elements 108. In some embodiments, the second shaft 104 does not include the first lumen 158 and is not configured to receive the first elongated shaft 102 therethrough.

Although FIGS. 5 and 6 depict a single second lumen 160 and a single aperture 162, the second shaft 104 can include multiple second lumens 160 and/or multiple apertures 132. For example, the second shaft 104 can comprise a first aperture 162 longitudinally spaced apart from a second aperture 162, with both the first and second apertures 162 being fluidically coupled to a single second lumen 160. In some embodiments, the second shaft 104 comprises a first aperture 162 circumferentially spaced apart from a second aperture 162. In such embodiments, the first and second apertures 162 can be fluidically coupled to a single second lumen 160 or the first aperture 162 can be fluidically coupled to a one second lumen 160 and the second aperture 162 can be fluidically coupled to another, radially adjacent second lumen 160. In some embodiments, for example as shown in FIG. 5, the second shaft 104 can define one or more channels 136 extending along the longitudinal axis L and positioned radially adjacent to the first and second lumens 158, 160. Each of the channels 136 can be configured to receive an elongate conducting element 168 having a distal end configured to be coupled to one or more conductive elements 108.

When the device 100 is inserted into the patient's pharynx and the conductive elements 108 are positioned at or adjacent a treatment site (see FIG. 6), the aperture 162 can be positioned within a treatment distance TD of the pharyngeal substance PS. As described herein with reference to the therapeutic region 140, when the aperture 162 is positioned within a treatment distance TD of the pharyngeal substance PS, the aperture 162 can be positioned at or adjacent the pharyngeal substance PS and/or in fluidic contact with the pharyngeal substance PS. For example, the aperture 162 can be configured to be located at or adjacent a portion of the patient's pharynx including a pooled pharyngeal substance such as the valleculae (see FIG. 5) or the pyriform sinuses.

In some embodiments, the device 100 is configured to aspirate the pharyngeal substance PS into the device 100 and out of the patient's body. The pressure source 134 can be configured to generate a negative pressure (i.e., suction) within the second lumen 160 to draw the pharyngeal substance into the aperture 162 and proximally through the second lumen 160 to the pressure source 134. In some embodiments, the pressure source 134 includes a container configured to collect the pharyngeal substance PS. Removing the pharyngeal substance PS from the patient's pharynx can prevent or reduce aspiration of the pharyngeal substance PS and thereby reduce the patient's risk of developing an airway infection. As pharyngeal substances PS may pool in a generally continuous manner, the device 100 may be used to aspirate pharyngeal substances PS multiple times while the device 100 is inserted into the patient. For example, in some embodiments the device 100 is used to aspirate pharyngeal substances PS once per day, twice per day, three times per day, or more. The device 100 may also be used to aspirate pharyngeal substances PS less frequently (e.g., once every other day, once per week, etc.).

In some embodiments, the device 100 is configured to deliver a fluid carrying the therapeutic agent to the pharyngeal substance PS via the second lumen 160 and aperture 162. The device 100 can include a reservoir containing the fluid, and the reservoir can be fluidically coupled to the second lumen 160. The pressure source 134 can be configured to generate a positive pressure within the second lumen 160 to push the fluid carrying the therapeutic agent distally through the second lumen 160 and out of the aperture 162 to the pharyngeal substance PS. As described herein, the therapeutic can have antimicrobial properties such that the therapeutic agent is configured to prevent or inhibit colonization of the pharyngeal substance PS by a pathogen. The aperture 162 can be positioned at or adjacent the pharyngeal substance PS and/or in contact with the pharyngeal substance PS such that the therapeutic agent is delivered directly to the pharyngeal substance PS. In some embodiments, the aperture 162 is positioned proximal of the pharyngeal substance PS such that the therapeutic agent travels distally through the patient's nasal cavity and/or pharynx to the pharyngeal substance PS. The fluid carrying the therapeutic agent can be delivered to the pharyngeal substance PS a single time or multiple times.

In some embodiments, the device 100 is configured to both aspirate pharyngeal substances PS and deliver fluid carrying the therapeutic agent to the pharyngeal substances PS. For example, in some embodiments it may be advantageous to first deliver the fluid carrying the therapeutic agent to the pharyngeal substance PS and then aspirate any excess fluid and pooled pharyngeal substance PS out of the patient. In some embodiments it may be advantageous to first aspirate a pharyngeal substance PS out of the patient and then deliver the fluid carrying the therapeutic agent. Still, in some embodiments the device 100 may be configured to perform only one of the above-noted functions.

Conclusion

Although many of the embodiments are described above with respect to systems, devices, and methods for electrically stimulating a pharynx of a patient to treat a patient suffering from dysphagia, the technology is applicable to other applications and/or other approaches. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

As used herein, the terms "generally," "substantially," "about," and similar terms are used as terms of approximation and not as terms of degree, and are intended to account for the inherent variations in measured or calculated values that would be recognized by those of ordinary skill in the art.

I claim:

1. A device for delivering an electrical stimulus to nerves proximate a body lumen of a human patient and preventing or reducing aspiration of a substance from the body lumen into an airway of the patient, the device comprising:

a pressure source;

a first elongated shaft;

a second elongated shaft having a proximal portion configured to be electrically coupled to an energy source and fluidically coupled to the pressure source and a distal portion configured to be positioned at or adjacent a treatment site within the body lumen, the second elongated shaft having a sidewall defining a first lumen configured to slidably receive the first elongated shaft therethrough, a second lumen, and an aperture extending radially between the second lumen and an outer surface of the second elongated shaft; and a conductive element carried by the distal portion of the second elongated shaft and configured to be electrically coupled to the energy source to deliver an electrical stimulus to nerves proximate the body lumen at the treatment site, wherein, when the first and second elongated shafts are positioned in the body lumen with the conductive element located at or adjacent the treatment site, the aperture is located within a treatment distance of the substance within the body lumen, and wherein the pressure source is configured to generate negative pressure within the second lumen to draw the substance into the aperture and proximally through the second lumen.

2. The device of claim 1, wherein the pressure source is configured to generate positive pressure within the second lumen to transport a fluid including a therapeutic agent distally through the second lumen and the aperture to the substance.

3. The device of claim 2, wherein the therapeutic agent is an antimicrobial agent configured to prevent or inhibit colonization of the substance by a pathogen.

4. The device of claim 1, wherein the body lumen comprises a pharynx of the patient.

5. The device of claim 4, wherein the substance is positioned within a recess of the patient's pharynx.

6. A device for delivering an electrical stimulus to nerves proximate a pharynx of a human patient and preventing or reducing aspiration of a substance from the pharynx into an airway of the patient, the device comprising:

a pressure source;

an elongated member having a proximal portion configured to be electrically coupled to an energy source and fluidically coupled to a pressure source and a distal portion configured to be positioned at or adjacent a treatment site within the pharynx, the elongated member having a sidewall defining a lumen therethrough and an aperture extending radially between the lumen and an outer surface of the elongated member; and a conductive element carried by the distal portion of the elongated member and configured to be electrically coupled to the energy source to deliver an electrical stimulus to nerves proximate the pharynx at the treatment site, wherein the aperture is disposed proximal of the conductive element along a longitudinal axis of the elongated member, wherein, when the elongated member is positioned in the pharynx with the conductive element located at or adjacent the treatment site, the aperture is located within a treatment distance of the substance within the pharynx, and wherein the pressure source is configured to generate a negative pressure within the lumen to draw the substance into the aperture and proximally through the lumen.

7. The device of claim 6, wherein the elongated member comprises a closed distal end.

8. The device of claim 6, wherein the substance is positioned within a recess of the patient's pharynx.

9. The device of claim 6, wherein the elongated member does not comprise a feeding tube.

10. The device of claim 6, wherein the nerves comprise a glossopharyngeal nerve.

11. The device of claim 6, wherein the elongated member comprises a therapeutic region at the distal portion, the therapeutic region containing a therapeutic agent configured to prevent or reduce colonization of the substance by a pathogen.

12. The device of claim 11, wherein the therapeutic region is configured to release the therapeutic agent when the therapeutic region is in mechanical or fluidic contact with the substance.

13. A device for delivering an electrical stimulus to nerves proximate a pharynx of a human patient and preventing or reducing aspiration of a substance from the pharynx into an airway of the patient, the device comprising:

an elongated member having a proximal portion configured to be electrically coupled to an energy source and fluidically coupled to a pressure source and a distal portion configured to be positioned at or adjacent a treatment site within the pharynx, the elongated member having a sidewall defining a lumen therethrough and an aperture extending radially between the lumen and an outer surface of the elongated member; and a conductive element carried by the distal portion of the elongated member and configured to be electrically coupled to the energy source to deliver an electrical stimulus to nerves proximate the pharynx at the treatment site, wherein the aperture is disposed proximal of the conductive element along a longitudinal axis of the elongated member, wherein, when the elongated member is positioned in the pharynx with the conductive element located at or adjacent the treatment site, the aperture is located within the pharynx adjacent the valleculae and/or pyriform sinuses, and wherein the pressure source is configured to generate a negative pressure within the lumen to draw the substance from the valleculae and/or pyriform sinuses into the aperture and proximally through the lumen.

14. The device of claim 13, wherein the elongated member comprises an open distal end.

15. The device of claim 13, wherein the elongated member comprises a closed distal end.

16. The device of claim 13, wherein the substance is positioned within a recess of the patient's pharynx.

17. The device of claim 13, wherein the elongated member does not comprise a feeding tube.

18. The device of claim 13, wherein the nerves comprise a glossopharyngeal nerve.

19. The device of claim 13, wherein the elongated member comprises a therapeutic region at the distal portion, the therapeutic region containing a therapeutic agent configured to prevent or reduce colonization of the substance by a pathogen.

20. The device of claim 13, wherein the elongated member comprises one or more visual markings.

* * * * *